United States Patent [19]
Schulz et al.

[11] Patent Number: 5,836,957
[45] Date of Patent: Nov. 17, 1998

[54] LARGE VOLUME ATHERECTOMY DEVICE

[75] Inventors: Grace Y. Schulz, San Carlos; Gerri Chatelain, Pleasanton; Mark E. Deem, San Francisco; Ferolyn T. Powell, San Carlos, all of Calif.

[73] Assignee: Devices For Vascular Intervention, Inc., Santa Clara, Calif.

[21] Appl. No.: 807,822

[22] Filed: Feb. 26, 1997

Related U.S. Application Data

[63] Continuation of Ser. No. 361,599, Dec. 22, 1994, abandoned.

[51] Int. Cl.$^6$ ..................................................... A61B 17/22
[52] U.S. Cl. .......................... 606/159; 606/167; 606/170; 606/192; 606/193; 606/194; 604/22; 604/96
[58] Field of Search .................................. 606/159, 167, 606/170, 171, 180, 192, 193, 195; 604/22, 96

[56] References Cited

U.S. PATENT DOCUMENTS

| | | | |
|---|---|---|---|
| 5,049,131 | 9/1991 | Deuss | 604/96 |
| 5,071,425 | 12/1991 | Gifford, III et al. | 606/159 |
| 5,087,246 | 2/1992 | Smith | 604/96 |
| 5,092,873 | 3/1992 | Simpson et al. | 606/159 |
| 5,147,302 | 9/1992 | Euteneuer et al. | 604/103 |
| 5,263,959 | 11/1993 | Fischell | 606/180 |
| 5,295,995 | 3/1994 | Kleiman | 606/194 |
| 5,350,361 | 9/1994 | Tsukashima et al. | 604/96 |
| 5,370,609 | 12/1994 | Drasler et al. | 604/22 |
| 5,409,454 | 4/1995 | Fischell et al. | 604/22 |
| 5,413,557 | 5/1995 | Solar | 604/96 |
| 5,458,572 | 10/1995 | Campbell et al. | 604/94 |
| 5,484,411 | 1/1996 | Inderbitzen et al. | 604/194 |
| 5,484,449 | 1/1996 | Amundson et al. | 606/108 |

FOREIGN PATENT DOCUMENTS

| | | | |
|---|---|---|---|
| 0414350 | 2/1991 | European Pat. Off. | 606/194 |
| 9217118 | 10/1992 | WIPO | 606/159 |

*Primary Examiner*—Michael Powell Buiz
*Assistant Examiner*—Daphna Shai
*Attorney, Agent, or Firm*—Heller, Ehrman, White & McAuliffe

[57] ABSTRACT

A side-cutting atherectomy catheter with a housing containing a tissue-removal means, a window on one side, and a large volume inflatable support on the opposite side. The large volume inflatable support has a maximum diameter larger than the diameter of the cutter housing, generating a greater degree of contact with a blood vessel's interior diameter than conventional balloon-housing configurations. This feature stabilizes the cutter housing and improves tissue-removal during the atherectomy procedure. Large volume inflatable supports have a maximum inflated diameter at least 1.1 times, and preferably 1.35 times, greater than the diameter of the housing. The supports may be formed from either elastic or inelastic materials. When formed from inelastic materials, the supports have slack material when uninflated which can extend into and become entangled with the cutter window. To prevent this problem, the large volume inflatable support is constrained when uninflated. The means for constraining the support generally comprises balloon structures, housing structures, or storage or shielding features. In a preferred embodiment, the large volume inflatable support comprises a balloon formed with a plurality of preferential longitudinal folds. When deflated, the folds cause the balloon to form an overlapping flap of material which constrains the slack balloon material from extending around the housing and becoming entangled in the cutter window.

19 Claims, 3 Drawing Sheets

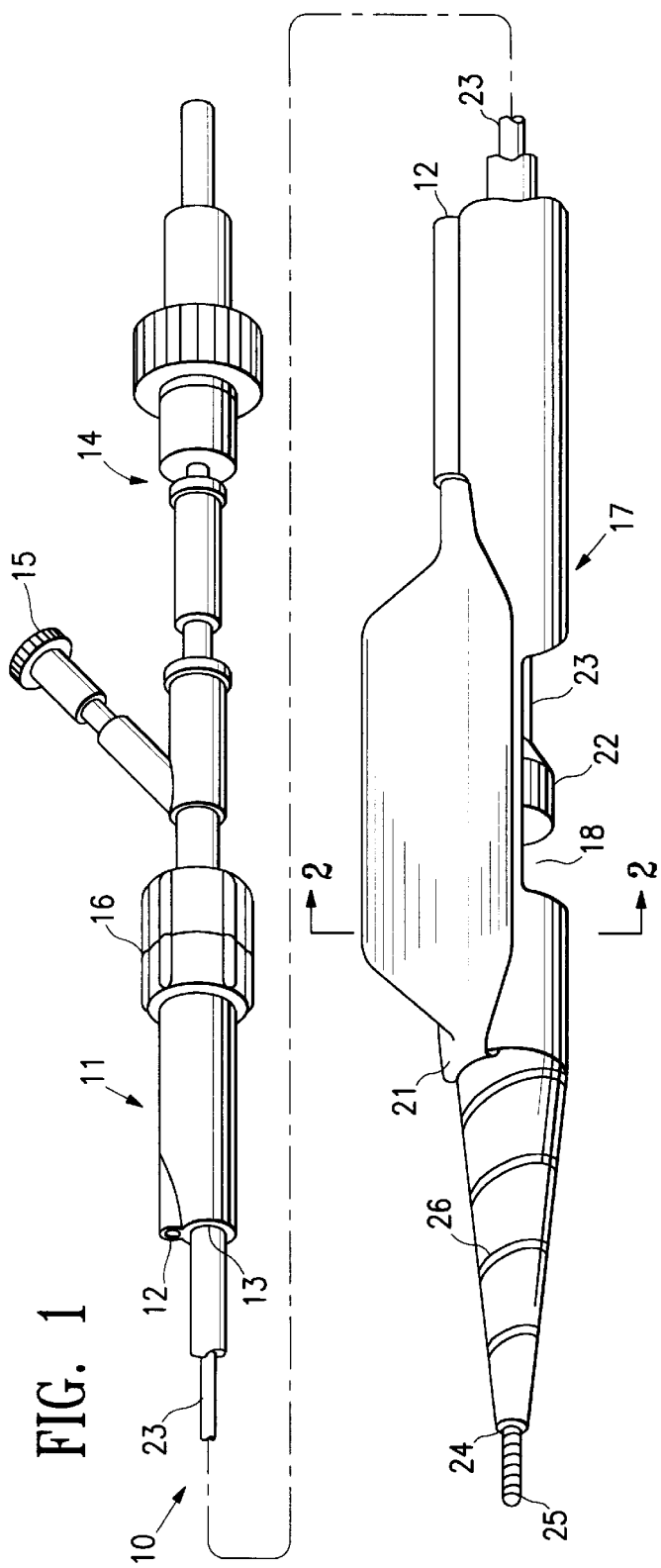
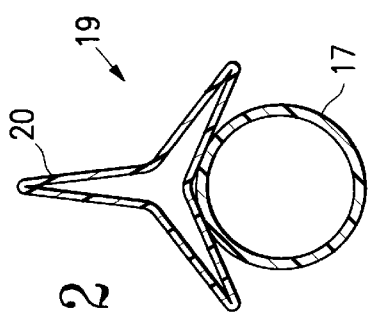
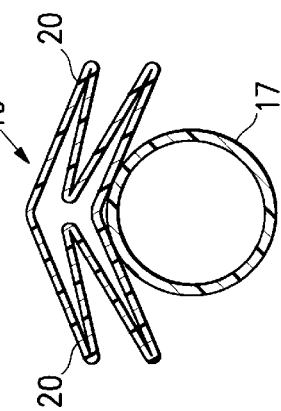

LARGE VOLUME ATHERECTOMY DEVICE

This is a continuation of application Ser. No. 08/361,599, which was filed on Dec. 22, 1994, now abandoned.

BACKGROUND OF THE INVENTION

The present invention is directed to the field of atherectomy catheters and in particular, to side-cutting atherectomy catheters using an inflatable balloon to support and position the cutting implement.

Arteriosclerosis is a common condition which occurs when atheromas, fatty-like substances, deposit in the blood vessels of a patient. Stenoses resulting from such deposits can seriously interfere with blood flow in the affected vessel, creating ischemic conditions distal to the stenosis. The use of intravascular catheters to remove stenotic material from a patient's vasculature is well known in the art. One type of widely used catheter is a side-cutting atherectomy catheter which has a cutting implement shielded in a housing with a longitudinal window and an inflatable balloon located opposite the window. Examples of such catheters are disclosed in U.S. Pat. Nos. 5,071,425 (Gifford, III et al.) and 5,092,873 (Simpson et al.) which are hereby incorporated in their entirety by reference thereto. When using these devices, the operator positions the housing across the lesion in a stenosed region of the patient's vessel and inflates the balloon to push the housing against the stenosis, causing stenotic material to extend through the window into the housing. The cutting implement then excises any stenotic material protruding into the housing. Additional stenotic material may be removed by deflating the balloon and torquing the catheter to reposition the housing with the window facing a different portion of the stenosis. Reinflating the balloon pushes the housing against that portion of the stenosis so that new material extends into the housing and may be excised. These steps are repeated until the region has been sufficiently revascularized.

Conventional side-cutting atherectomy catheters have a balloon with an inflated diameter approximately the same as the housing's diameter. In use, the transverse balloon-housing configuration is basically oval. Since blood vessels are generally circular in cross-section, an oval balloon-housing configuration contacts the vessel at only two locations. This configuration has inherent instability problems and decreases the tissue-removal capability of the catheter. What has been needed, and heretofore unavailable, is an atherectomy catheter with a balloon-housing configuration that contacts a greater portion of the blood vessel during use to improve stability and tissue-removal.

SUMMARY OF THE INVENTION

The atherectomy catheters of this invention comprise a flexible catheter shaft with a proximal end and a distal end. At the distal end of the shaft is a cylindrical housing with a window on one side and an inflatable support located on the opposite side. Means for excising stenotic tissue is disposed within the interior of the housing and is configured to cut stenotic material extending through the window into the housing interior.

The catheters of this invention employ a large volume inflatable support, comprised of a single balloon or a plurality of balloons, which has a maximum inflated diameter larger than the housing's diameter to provide improved support to the housing during the atherectomy procedure. The resulting transverse balloon-housing configurations generate a greater degree of contact with a blood vessel's interior diameter than conventional side-cutting catheters. Thus, the balloon-housing configurations of this invention are more stably positioned within a blood vessel when inflated. Correspondingly, tissue-removal capabilities are improved because the large volume inflatable support pushes the housing more solidly against the stenosis which causes more of the atheroma to extend through the window. The stable platform provided by the large volume inflatable support also helps keep the stenotic material positioned within the window during the cutting operation.

The maximum inflated diameter of the large volume support should be at least 1.1, preferably at least 1.35, times the diameter of the housing. The large volume inflatable support may be formed of many suitable materials already found useful in this field and in the field of dilatation catheters. Common examples of these materials include nylon, polyethylene, polyethylene terephthalate and ionomers such as Surlyn™. Generally, these materials may be either elastic (compliant) or inelastic (non-compliant).

During use, the operator positions the housing across a lesion in a stenosed region of the patient's vasculature by conventional means, including an introducing catheter, a guiding catheter and a guidewire, for example. Once the catheter is positioned, the operator inflates the support to push the housing against the stenosis and cause stenotic material to enter the housing interior to be severed. After removing that portion of the stenotic material, the operator deflates the inflatable support and torques the catheter shaft to reposition the cutter window against a different section of the stenosis.

Since the inflated circumference of the large volume inflatable supports of this invention must be larger than the circumference of the housing, the slack support material when uninflated potentially can extend or "roll" around the housing and become entangled in the cutter window. An inflatable support may exhibit roll when the ratio of inflatable support diameter to housing diameter exceeds about 1.1. When formed from an elastic material, the large volume inflatable support exhibits little or no slack material when uninflated and poses no problem. However, the use of large volume inflatable supports formed from inelastic material requires features not found in conventional balloon/housing configurations to prevent the slack balloon material from becoming entangled in the cutter window. This invention enables the use of inflatable supports which are large enough to become entangled in the cutter window but are stabilized, constrained or exhibit other "anti-roll" characteristics to prevent entanglement.

This invention comprises a number of embodiments which exhibit anti-roll properties. Generally, these embodiments have features which fall into three categories: balloon structures which provide the anti-roll constraint; housing structures which provide the constraint; and storage or shielding structures which protect the inflatable support when uninflated. A preferred embodiment comprises a large volume balloon with preferential longitudinal folds. When the balloon is deflated, the folds cause an overlapping flap to form which prevents the balloon material from extending around the housing and entering the cutter window.

Other benefits accrue from the use of large volume inflatable supports in addition to improved stability and tissue retrieval capabilities. The use of a large volume inflatable support increases the range of vessel sizes that may be treated with a particular catheter. A smaller housing may be used to treat a given vessel diameter which consequently reduces trauma to the vessel and facilitates positioning of the catheter. The large volume inflatable supports of this invention also may be configured to perform angioplasty dilatation procedures either before or after the atherectomy.

BRIEF DESCRIPTION OF THE DRAWINGS

FIG. 1 is an elevational view of an atherectomy catheter having features of the invention.

FIG. 2 is a transverse cross-sectional view taken at the line 2—2 in FIG. 1 showing the tri-fold triangular balloon configuration.

FIG. 3 is a transverse cross-sectional view of an alternate embodiment showing a quad-fold balloon configuration.

DETAILED DESCRIPTION OF THE INVENTION

Figure 4:
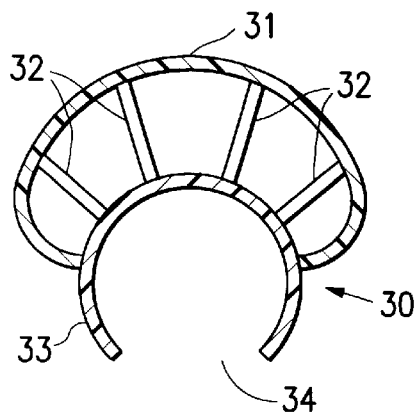
FIG. 4 is a transverse cross-sectional view of an alternate embodiment showing a balloon with struts.

FIG. 1 illustrates an atherectomy catheter 10 which generally includes a flexible catheter shaft 11 having proximal and distal ends, an inflation lumen 12, and a drive lumen 13. An adaptor 14 has a side arm 15 adapted to direct inflation fluid through the inflation lumen 12 and is connected at the proximal end of catheter shaft 11 by a conventional rotatable fitting 16. Secured to the distal end of catheter shaft 11 is an elongate housing 17. Depending on the application, the housing 17 may be formed from rigid or flexible material. The housing 17 has an elongate cutter window 18 formed on one side. Secured to the housing 17 on the side opposite the cutter window 18 and in fluid communication with inflation lumen 12 is a balloon 19, a large volume inflatable support embodying features of this invention.

Balloon 19 is formed with three preferential longitudinal folds to form a triangular tri-fold configuration as shown in FIG. 2. When deflated, the balloon forms a flap 20 which folds back on itself. Because the balloon material overlaps, there is insufficient slack material to roll around the housing and get caught in the cutter window. This configuration can be formed by conventional means including placing a piece of suitable tubing in a triangular mold, pressurizing the tubing and heating the mold to expand the tubing. Evacuating the balloon after cooling it forms the tri-fold triangular configuration. Other techniques for producing folded balloons to provide a low profile are well-known in the angioplasty field and are disclosed in U.S. Pat. Nos. 5,087,246 (Smith) and 5,147,302 (Euteneuer et al.) which are incorporated herein in their entirety by reference thereto. For this invention, the folding techniques enable the use of a balloon as a large volume inflatable support by constraining the balloon's movement when deflated. One side of the balloon 19 may additionally comprise a longitudinal rounded indentation to conform to the exterior of housing 17.

Other configurations which may have different folding patterns and different numbers of preferential folds are also possible. FIG. 3 illustrates a quad-fold anvil configuration of balloon 19 which forms two overlapping flaps 20.

The balloon 19 may be a separate member formed from suitable materials such as polyethylene, polyethylene terephthalate and ionomers such as Surlyn™, particularly from materials capable of biaxial orientation, or may be an integral portion of catheter shaft 11, formed by expanding a distal portion of inflation lumen 12. Balloon 19 may be secured to housing 17 by any suitable means. Preferably, a tab 21 may be formed at the distal end of balloon 19 by compressing a portion of the balloon material in a heated platen. Tab 21 may be formed so that a portion of the folded flap 20 is also compressed in the platen to facilitate the balloon's return to a tri-fold configuration when deflated. The tab is tucked into the distal end of the housing 17 in order to secure the balloon. Greater anti-roll constraint can be achieved by tucking in more of the distal end of the balloon so that a larger proportion of the maximum diameter of the balloon is secured. The proximal end of the balloon may be secured to the distal end of the catheter shaft 11 and the proximal end of the housing 17 by heatshrinking a suitable plastic tubing, such as Surlyn®, over the assembly. The length of balloon 19 may be secured to housing 17 by an adhesive, particularly a cyanoacrylate based adhesive.

Disposed within housing 17 is cutting means 22 which moves axially across cutter window to excise stenotic material disposed within the housing 17. The cutting means 22 shown is a rotatable blade, but many other means for removing stenotic material are suitable, including, but not limited to, radiation generating, drilling, abrading, shearing, etc. Cutting means 22 is connected to drive means 23 which is disposed within drive lumen 13. Drive means 23 extends through the catheter shaft 11, extends out adaptor 14 and is connected to drive operating means (not shown). When the cutting means 22 is a rotatable cutting means, drive means 23 generally comprises a multistrand metal braid and additionally may be formed as a tube and lined with a suitable plastic to form a guidewire receiving lumen 24 in which guidewire 25 is slidably disposed. A conventional flexible, open-ended tip 26 is secured to the distal end of housing 17.

Catheter shaft 11 generally is formed from materials already found useful in intravascular catheters such as polyethylene, polyvinyl chloride, and polyesters or polyester-polyamides such as Hytrel®. The catheter shaft may be reinforced with suitable materials such as braided stainless steel or other metals or carbon fiber in order to improve torque transmission.

The method of using the catheters of this invention generally follows conventional practices. In particular, the catheter shown in FIG. 1 may be located by first introducing a guiding catheter (not shown) having a preshaped distal tip percutaneously in the patient's arterial system using the conventional Seldinger technique and advancing it until the preshaped distal tip is seated in the ostium of the desired artery. A guidewire 25 is backloaded into guidewire receiving lumen 24, and both the guidewire and the atherectomy catheter are advanced together through the guiding catheter to its distal end. The guidewire 25 is advanced out the guiding catheter through the patient's vasculature via fluoroscopic imaging until it crosses the target lesion. Then the atherectomy catheter 10 is advanced over the guidewire 25 until the housing 17 is positioned across the lesion. The balloon 19 is inflated to urge the housing 17 against the stenotic tissue so that atheroma extends through the cutter window 18. The cutter 22 excises the portion of the stenosis protruding into the housing 17. The balloon 19 then may be deflated and the catheter shaft 11 torqued by rotating rotatable fitting 16 to reposition the housing within the stenotic region to remove additional atheroma. The tri-fold configuration of balloon 19 causes a flap 20 of the slack balloon material to fold back on itself, preventing the balloon material from rolling into the cutter window 18. Torquing the catheter shaft repositions cutter window 18 adjacent an unexcised portion of the stenosis. The above steps are repeated until the vessel has been sufficiently revascularized to minimize ischemic conditions distal to the stenotic region.

A number of other balloon configurations provide anti-rolling properties. Referring to FIG. 4, an alternate balloon-housing configuration 30 is shown which embodies features of this invention. The large volume inflatable support is a balloon 31 having additional struts 32 to stabilize and prevent the balloon material from extending around the housing 33 and reaching the cutter window 34. Alternately, the struts can run longitudinally from the proximal end to the distal end of the balloon to form a multilumen balloon (not shown).

Figure 5:
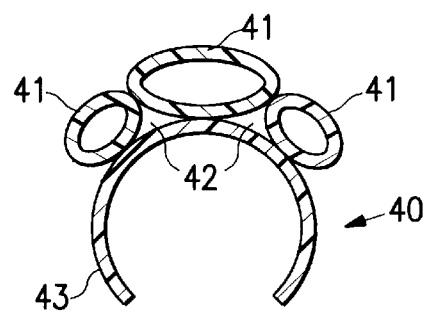
FIG. 5 is a transverse cross-sectional view of an alternate embodiment showing multiple balloons and perfusion lumens.

FIG. 5 illustrates an balloon-housing configuration 40 where the large volume inflatable support comprises a plurality of separate balloons 41. A similar arrangement is disclosed in U.S. Pat. No. 5,071,425 (Gifford, III et al.) which has already been incorporated by reference. The smaller individual circumferences of the balloons prevent any one of them from rolling into the cutter window. The balloons may be secured to the housing and to each other by any suitable means, including cyanoacrylate based adhesives. Preferably, this configuration results in the formation of lumens 42 between the balloons 41 and the housing 43. These lumens provide perfusion capability when balloons 41 are inflated.

Figure 6:
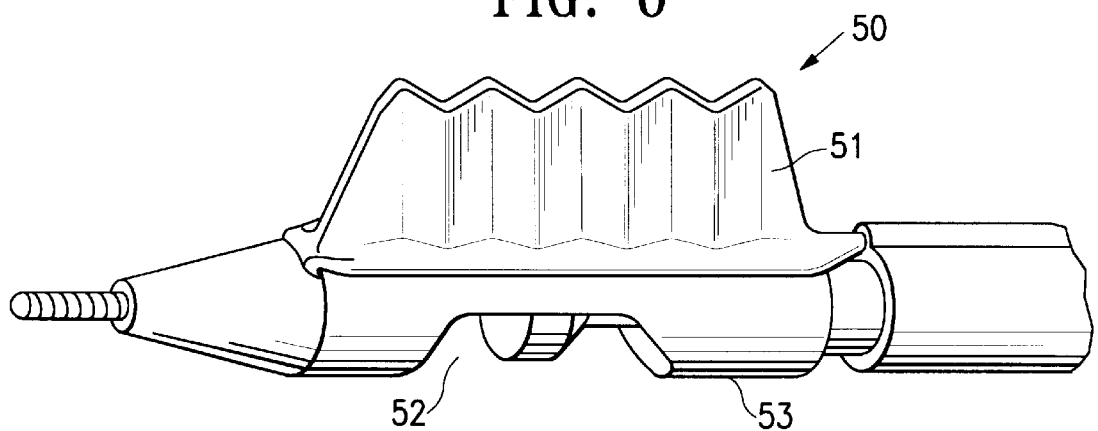
FIG. 6 is an elevational view of an alternate embodiment showing preferential latitudinal folds.

Another embodiment having features of this invention is shown in FIG. 6. Generally, balloon 50 has a plurality of latitudinal preferential folds 51 in a pleat arrangement. The folds 51 prevent the balloon 50 from rolling into the cutter window 52. Housing 53 is preferably formed from a flexible material. The pleat configuration allows balloon 50 to follow the contours of the flexible housing 53.

Figure 7:
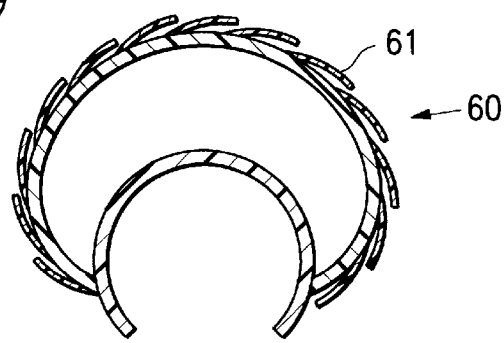
FIG. 7 is a transverse cross-sectional view of an alternate embodiment showing a balloon having strips of coating material.

FIG. 7 illustrates an embodiment of this invention which generally comprises a balloon 60 with strips 61 formed of a coating material. The material keeps the balloon rigid, preventing it from rolling during torquing. Strips 61 either overlap or are adjacent one another. Strips 61 also protect balloon 60 from abrasion when treating calcified atheromas.

Figure 8:
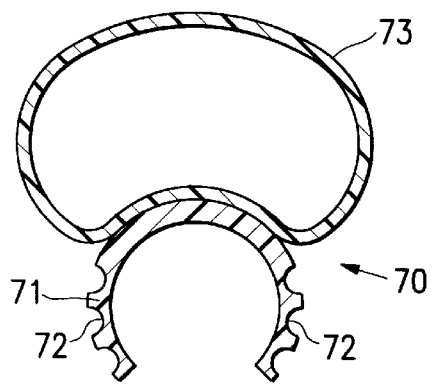
FIG. 8 is a transverse cross-sectional view of an alternate embodiment showing longitudinal grooves in the housing.
Figure 9:
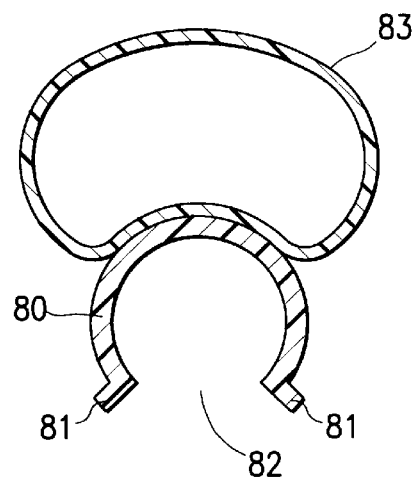
FIG. 9 is a transverse cross-sectional view of an alternate embodiment showing a ridge around the cutter window.

Specific features on the housing also can provide anti-roll properties. For example, FIG. 8 illustrates a balloon-housing configuration 70 embodying features of this invention. Housing 71 has a series of longitudinal grooves 72 on the outside diameter to catch and restrain balloon 73. A variation is shown in FIG. 9, which illustrates a housing 80 having an external ridge 81 at cutter window 82 to catch the balloon 83 before it enters window 82.

Figure 10:
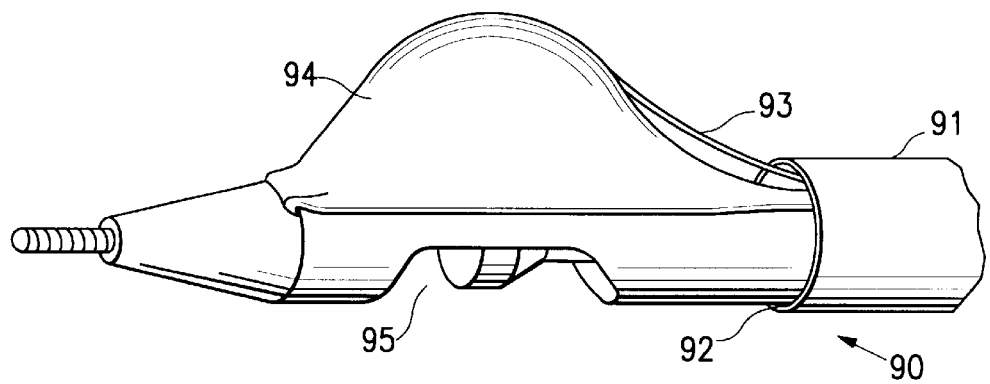
FIG. 10 is an elevational view of an alternate embodiment showing balloon storage in the catheter shaft.

Other embodiments comprise features on the housing or catheter which shield the balloon when uninflated. In the embodiment shown in FIG. 10, catheter shaft 90 further comprises a protective sheath 91 which forms annular lumen 92. A leash 93, attached to balloon 94, extends from the balloon 94, through annular lumen 92 to the proximal end of catheter shaft 90 and out the adaptor (not shown). When balloon 94 is deflated, leash 93 may be used to pull a portion of the balloon material into the protective sheath 91 at the distal opening of annular lumen 92. The take-up of excess material prevents the balloon 94 from rolling into the cutter window 95.

Figure 11:
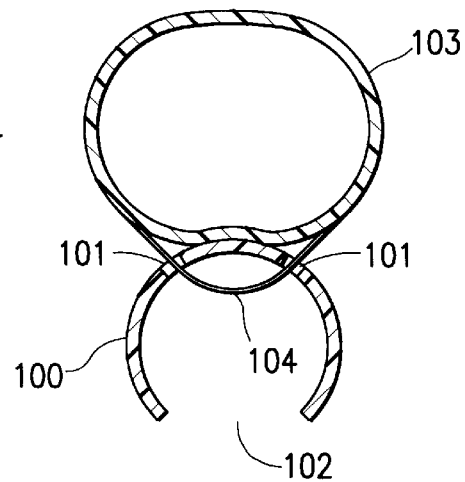
FIG. 11 is a transverse cross-sectional view of an alternate embodiment showing balloon storage in the housing.

Referring to FIG. 11, an alternative embodiment is shown which generally comprises a housing 100 with two longitudinal slots 101 located on the side opposite cutter window 102. Balloon 103 enters housing 100 through the slots 101. A leash 104, disposed within housing 100 and extending through the drive lumen (not shown) to the proximal end of catheter shaft (not shown), is attached to the portions of balloon 103 extending into housing 100. Tension applied to leash 104 pulls slack balloon material into housing 100 and prevents this material from rolling into cutter window 102. Other embodiments have tensioning means attached to the portions of the balloon extending into the housing. Any suitable means for applying tension to the slack balloon material are possible, including but not limited to compliant material or another balloon which, when inflated, acts to pull slack balloon material into the housing.

Other embodiments comprise a means for storing the rolled-up balloon in the housing or the catheter shaft. A leash extending to the proximal end of the catheter can be used to unfurl the balloon prior to inflation and can be detensioned to allow the balloon to reroll after deflation. In one example of this general embodiment, a balloon is rolled around spring-loaded axle and disposed within the housing. A leash attached to the proximal end of the balloon can unfurl the balloon prior to inflation. Likewise, after deflation, removing tension from the leash will allow the spring-loaded axle to reroll the balloon. This prevents the balloon from becoming entangled in the cutter window during catheter torquing. As suggested, several variations are possible employing this general concept. In another embodiment, the balloon is stored in the catheter shaft or the proximal end of the housing. Optionally, the balloon can cover substantially the entire housing for performing angioplasty procedures.

The invention has been described herein primarily with reference to presently preferred embodiments. However, it should be recognized that various modifications and improvements can be made to the invention without departing from the scope thereof.

What is claimed is:

1. An atherectomy catheter comprising:
   a) a catheter shaft having a proximal end, a distal end and an inflation lumen extending therein;
   b) an elongated housing at the distal end of the catheter shaft having an inner chamber and a window in fluid communication with the inner chamber in a wall portion of the elongated housing;
   c) means for cutting stenotic material which extends through the window into the inner chamber of the housing;
   d) an elongated large volume inflatable support which is secured to the housing on a side thereof opposite the window, which is in fluid communication with the inflation lumens, which has an effective diameter when inflated such that the ratio of the effective diameter thereof to the diameter of the elongated housing is at least about 1.1:1 and which has an unsecured portion radially constrained only toward the side of the housing opposite the window when uninflated to prevent the unsecured portion of the uninflated large volume inflatable support from extending through the window into the inner chamber of the elongated housing.

2. The atherectomy catheter of claim 1 wherein the ratio of the effective diameter of the large volume inflated support to the diameter of the elongated housing is at least about 1.35.

3. The atherectomy catheter of claim 1 wherein the large volume inflatable support is formed from inelastic material.

4. The atherectomy catheter of claim 1 wherein the large volume inflatable support comprises a balloon and a constraining means for constraining the large volume inflatable support which comprises a plurality of substantially longitudinal preferential folds formed in an unsecured portion of the balloon.

5. The atherectomy catheter of claim 4 wherein the preferential longitudinal folds are configured to produce a tri-fold triangular configuration which forms an overlapping flap when the large volume support is in an uninflated condition.

6. The atherectomy catheter of claim 5 wherein the tri-fold triangular configuration further comprises a longitudinal rounded indentation configured to conform to a portion of the elongated housing.

7. The atherectomy catheter of claim 4 wherein the preferential longitudinal folds are configured to produce a quad-fold configuration which forms two overlapping flap when the large volume support is in an uninflated condition.

8. The atherectomy catheter of claim 7 wherein the quad-fold configuration further comprises a longitudinal rounded indentation configured to conform to a portion of the elongated housing.

9. The atherectomy catheter of claim 1 wherein the large volume inflatable support comprises a balloon and a constraining means for constraining the large volume inflatable support which comprises a plurality of substantially latitudinal folds formed in the balloon.

10. The atherectomy catheter of claim 9 wherein the housing is configured to conform to curvature in a body lumen.

11. The atherectomy catheter of claim 1 wherein the large volume inflatable support comprises a balloon and a constraining means for constraining the large volume inflatable support comprises a number of struts disposed within the balloon, wherein each strut has opposing ends and each end is connected to non-adjacent points on the balloon.

12. The atherectomy catheter of claim 1 wherein the large volume inflatable support and the constraining means for constraining the large volume inflatable support comprises a plurality of balloons.

13. The atherectomy catheter of claim 13 further comprising a number of perfusion lumens, wherein each perfusion lumen is formed by two adjacent balloons and the housing.

14. The atherectomy catheter of claim 1 wherein the large volume inflatable support comprises a balloon and a constraining means for constraining the large volume inflatable support which comprises a plurality of strips of coating material secured to the balloon.

15. The atherectomy catheter of claim 1 wherein a constraining means for constraining the large volume inflatable support comprises a plurality of longitudinal grooves formed in the elongated housing configured to restrain the large volume inflatable support.

16. The atherectomy catheter of claim 1 wherein a constraining means for constraining the large volume inflatable support comprises a ridge formed around the elongated window configured to restrain the large volume inflatable support.

17. The atherectomy catheter of claim 1 wherein the large volume inflatable support comprises a balloon and a constraining means comprises a balloon storage means for constraining the large volume inflatable support.

18. The atherectomy catheter of claim 17 wherein the balloon storage means comprises a storage lumen in the catheter shaft and a tension supplying means connected to the balloon and disposed within the storage lumen.

19. The atherectomy catheter of claim 17 wherein the balloon storage means comprises a storage lumen in the housing and a tension supplying means connected to the balloon and disposed within the storage lumen.

* * * * *